United States Patent
Regan et al.

(10) Patent No.: US 8,137,285 B1
(45) Date of Patent: Mar. 20, 2012

(54) MONOPOLAR STIMULATION PROBE SYSTEM

(75) Inventors: Shawn V. Regan, Columbia, SC (US); Isiah Daniel Smith, Lexington, SC (US); James M. Mewborne, Swansea, SC (US); Brett L. Netherton, Prosperity, SC (US)

(73) Assignee: Rhythmlink International, LLC, Columbia, SC (US)

( * ) Notice: Subject to any disclaimer, the term of this patent is extended or adjusted under 35 U.S.C. 154(b) by 95 days.

(21) Appl. No.: 12/547,852

(22) Filed: Aug. 26, 2009

Related U.S. Application Data

(60) Provisional application No. 61/091,831, filed on Aug. 26, 2008.

(51) Int. Cl.
*A61B 5/05* (2006.01)

(52) U.S. Cl. ........................................ 600/554

(58) Field of Classification Search ............ 600/132, 600/133, 372, 547, 554; 606/32; 607/117, 607/118, 149
See application file for complete search history.

(56) References Cited

U.S. PATENT DOCUMENTS

| | | | |
|---|---|---|---|
| 5,042,482 A * | 8/1991 | Blumenfeld et al. ......... | 600/373 |
| 5,885,219 A | 3/1999 | Nightengale | |
| 6,533,732 B1 * | 3/2003 | Urmey ........................... | 600/554 |
| 6,618,626 B2 | 9/2003 | West, Jr. et al. | |
| 6,925,333 B2 | 8/2005 | Krebs | |
| 7,206,641 B2 | 4/2007 | Ignagni et al. | |
| 7,207,949 B2 | 4/2007 | Miles et al. | |
| 7,282,033 B2 | 10/2007 | Urmey | |
| 7,462,162 B2 | 12/2008 | Phan et al. | |
| 7,522,953 B2 | 4/2009 | Kaula et al. | |
| 7,553,307 B2 | 6/2009 | Bleich et al. | |
| 2005/0070895 A1 * | 3/2005 | Ryan et al. ..................... | 606/48 |
| 2005/0075578 A1 | 4/2005 | Gharib et al. | |
| 2005/0182454 A1 | 8/2005 | Gharib et al. | |
| 2006/0025702 A1 * | 2/2006 | Sterrantino et al. .......... | 600/554 |
| 2007/0021682 A1 * | 1/2007 | Gharib et al. ................. | 600/546 |
| 2007/0179508 A1 * | 8/2007 | Arndt ............................ | 606/116 |
| 2009/0018610 A1 | 1/2009 | Gharib et al. | |
| 2009/0192403 A1 | 7/2009 | Gharib et al. | |

* cited by examiner

*Primary Examiner* — Max Hindenburg
*Assistant Examiner* — Charles Becker
(74) *Attorney, Agent, or Firm* — Michael A. Mann; Nexsen Pruet, LLC

(57) ABSTRACT

A probe system for use with a neuro-monitoring device includes a wire probe, a cable and a handle. The cable has an adaptor at one end that is pressed from the side of the handle into an adaptor-shaped portion of a channel formed in the handle. The channel runs the length of the handle. The wire probe has a probe tip on one end and is in electrical connection with the adaptor on the other end when that adaptor end is inserted into the channel of the handle and seated in the adaptor held by the handle. The sensor tip on the end of the wire probe is a conducting, smooth, hemisphere just beyond the end of the insulation covering wire probe and conducts signals between the tissue through which the probe passes and the cable. The handle has ribs formed thereon for giving the user better purchase on the probe for applying the requisite force and control, and windows formed along the sides of the handle to allow the user to confirm that the wire probe is fully seated in the adaptor.

18 Claims, 3 Drawing Sheets

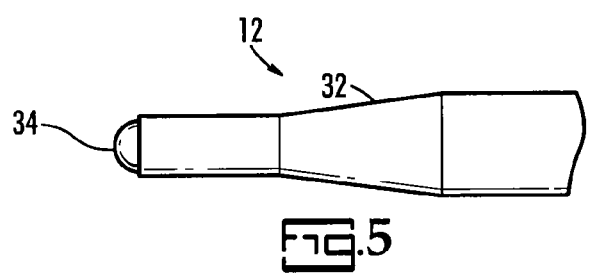
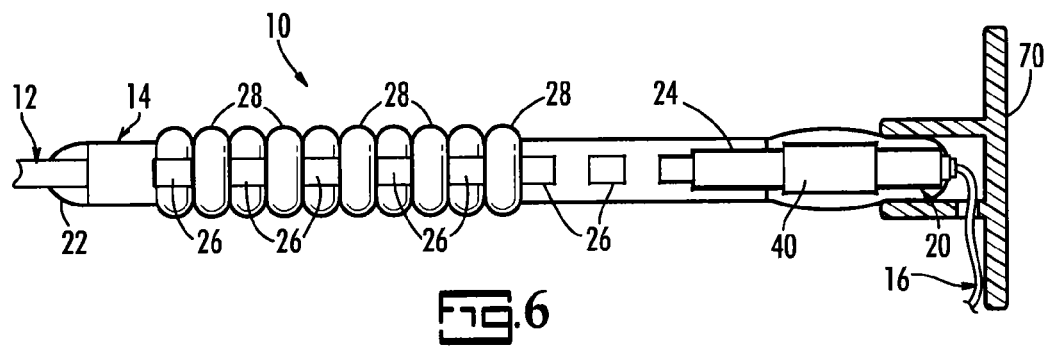

MONOPOLAR STIMULATION PROBE SYSTEM

PRIORITY CLAIM

Priority is claimed to U.S. provisional patent application 61/091,831, filed Aug. 26, 2008, which is incorporated herein in its entirety by reference.

Electrical probes are finding more and more uses in medical procedures, most commonly in intra-operative monitoring. A probe can be connected to a source of electrical potential and be used to locate nerves in the patient or to determine the connections between nerves and the parts of the body they service. Probes are used, for example, in thyroid surgery, parotidectomy, acoustic neuroma surgery, brain and brainstem surgery, and surgery involving the spinal cord. Probes are particularly useful in surgery to help identify neural tissue from non-neural tissue such as tumor, scar tissue, normal non-neural tissue.

A particular type of probe is called a monopolar probe. When a monopolar probe is used, the current (or voltage) flows from the tip of the stimulation probe in all directions. Whether a response from a nerve is obtained depends on the distance to the nerve from the tip of the probe, the impedance of the tissue between the tip of the probe and the nerve, and the strength of the electrical stimulus, the health and integrity of the stimulated nerve, the appropriate recording paradigm, and additional factors. Monopolar stimulators are used most often in lumbar spine procedures and ear-nose-throat procedures, tumor resection procedures, and cranial nerve monitoring. The size and shape of the probe will vary to suit the nature of the use.

Electrical monopolar stimulation probes are typically also in spinal cord surgery to identify spinal and other nerves and to evaluate the correct placement of pedicle screws. Typically, during minimally invasive and endoscopic surgical approaches the probe needs to be a long probe that is inserted into the patient's side between or below the ribs and directed toward the spinal cord. The probe can be inserted through the surgical wound directly or via the endoscopic tubes or other access methods. Because of the distance the probe needs to travel and the inevitable resistance provided by tissue between the entrance and the target location, it is important for the physician to be able to maneuver it precisely along the way and to know when the probe tip is near the target within the spinal cord.

Accordingly, because of the sensitive and delicate nature of the procedures with which monopolar stimulating probes are used, there remains a need for improvements to such probes to make them easier to work with and more effective in locating their targets without injury to the patient.

SUMMARY OF THE INVENTION

The present invention is a monopolar stimulation probe system that may be provided in kit form. The present probe system is for monopolar stimulation of tissues and nerves to locate tissues and nerves as part of a surgerical procedure.

The probe system includes an insulated, electrically isolated, rigid, probe wire having two ends, a first end serving as the probe tip and the second, opposing end being inserted into a channel formed in a specially-configured handle. The handle securely holds the first end in electrical connection to an adaptor on a first end of a cable. The opposing second end of the cable runs to a connector that can be plugged into a neuro-monitoring device. Current can then flow from the neuro-monitoring device through the connector and cable to the adaptor in the handle and then into the probe and to the probe tip.

The handle holds the adaptor securely. It also provides a more secure gripping surface for the user, particularly when the present probe is being passed through several inches of human tissue. It may also provide a flat, terminal end for tapping the probe wire into tissue. The handle is configured to allow the adaptor to be easily inserted into the handle from the side where the adaptor is locked in place against axial movement, that is, movement parallel to the long dimension of the handle, and helps to hold the probe wire in position axially by resisting movement rearward, in the direction opposite the direction the probe is being advanced into the patient's tissue. Also, a series of "windows" along the sides of the handle allow the user to see the end of the probe wire as it advances toward and seats in the adaptor when the present probe system is being assembled.

An important feature of the present invention is the ease with which the components of the probe system are assembled. With the handle in one hand, the user presses the adaptor into an adaptor-configured portion of the handle's channel from the side. Then the second end of the wire probe in inserted into the channel in the end of the handle and advanced rearward until it seats in the adaptor. The end of the cable opposite the adaptor can then be plugged into a neuro-monitoring device. Disconnection of the electrical connection between the probe and the neuro-monitoring device is simply a matter of sliding the probe from the adaptor and out of the channel in the handle.

An important feature of the present invention is the rippled surface of the handle. The rippled handle enables the user to get a better purchase on it for driving the long probe through the tissue of the patient with both sufficient force and finer control. The series of openings along the front and back also allow the user to verify that the probe wire is seated in the adaptor, as well as to see that the probe wire has seated in the adaptor. Finally, the portion of the channel configured to receive the adaptor from the side of the handle allows not only quicker assembly, but securer hold of the adaptor even under the pressure of the insertion of the probe tip through tissue.

Other features and their advantages will be apparent to those skilled in the art of monopolar stimulation probe design from a careful reading of the Detailed Description of Preferred Embodiments accompanied by the following drawings.

BRIEF DESCRIPTION OF THE DRAWINGS

In the figures,

FIG. 5 is a detailed view of the probe wire tip, according to a preferred embodiment of the present invention; and FIG. 6 is a view of an alternative preferred embodiment of the handle shown in FIG. 3A.

DETAILED DESCRIPTION OF PREFERRED EMBODIMENTS

Figure 1:
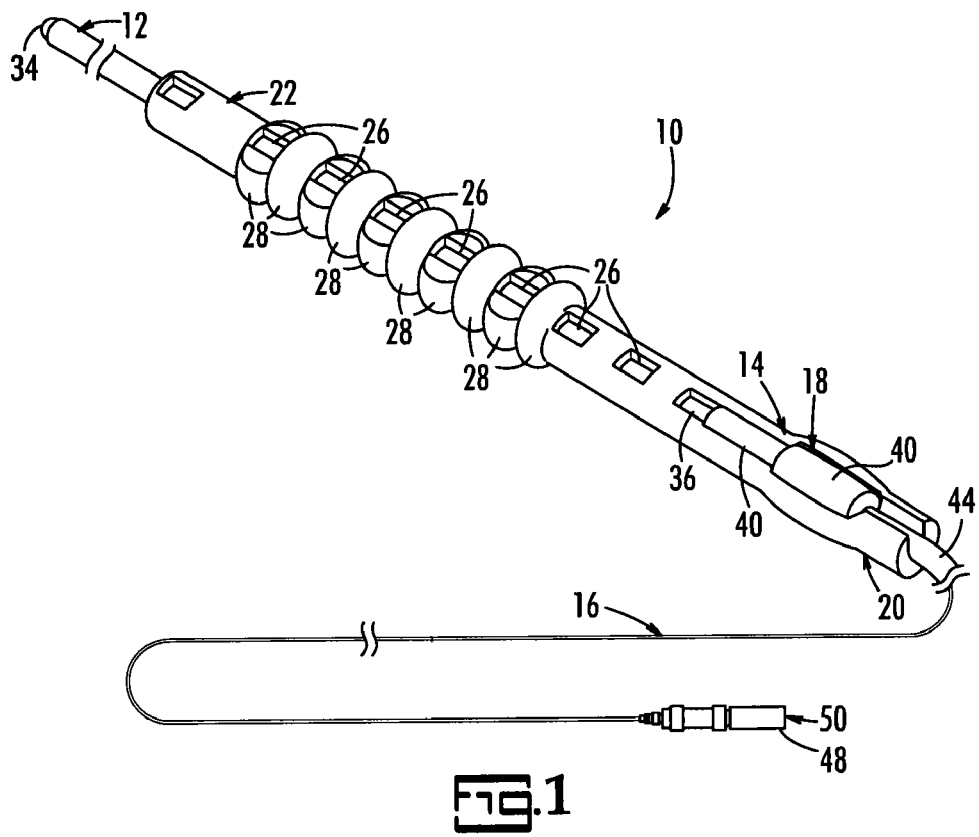
FIG. 1 is a perspective view of the monopolar stimulation probe system, according to a preferred embodiment of the present invention.

The present invention is a monopolar stimulating probe system, generally referred to by reference number 10. Probe system 10 includes a wire probe 12, a handle 14, and a cable 16 for use with a neuro-monitoring device 100. The present probe system may be sold in the form of a sterile kit, as will be described below.

Referring now to the figures, FIGS. 1-5 illustrate the present probe system 10 in a preferred embodiment. Probe system includes wire probe 12, handle 14 and cable 16. Handle 14 has a first end 22 and a second end 20. First end receives probe 14; second end receives cable 16. A channel 24 is formed axially in handle 14, along its full length from first end 22 to second end 20. Channel 24 has a shaped portion 18 at second end 20 to receive a cable adaptor 40. From shaped portion 18 at second end 20 to first end 22, a series of openings or "windows" 26 are formed on the top and bottom of handle 14 to allow the user to see into channel 24. Channel 24 is otherwise closed radially and thus secures wire probe 12 from movement in other than the axial direction, that is, co-axial with channel 24. The exterior surface of handle 14 includes a set of ribs 28 that allow the user to obtain a better purchase on handle 14 and to enable the user to find a comfortable gripping position on the exterior surface.

Preferably, set of ribs 28 includes a set of radial variations or bulges that are staggered with alternating bulges being offset from the long axis of handle. Windows 26 also alternate so that a window 26 formed in a bulge at the top of handle 14 is followed axially by a window 26 at the next bulge at the bottom of handle 14. While this exact surface configuration of handle 14 is not required, an effective surface configuration for allowing the surgeon non-slip control and, moreover, the ability to apply well-controlled axial force to handle 14 that is transmitted efficiently to wire probe 12 is critical. The present configuration provides good contact with the gloved fingers of the surgeon by providing variations in diameter along the axial length of probe 12 for better, more comfortable finger grip and for the application of controlled, non-slip, axial force. The use of windows 26 allows the surgeon to visually confirm that wire probe 12 is fully seated in adaptor 40.

Wire probe 12 is a thin but rigid electrical conductor 30, preferably made of steel, most preferably made of stainless steel, such as 316 stainless steel, with an insulating layer 32 made of a non-conductor, such as parylene C, a chemical vapor-deposited poly(p-xylylene) polymer.

The type of wire for probe 12 may be K-wire. K-wire is well-known in surgery such as, for example, holding bone fragments together, providing anchors for traction, and serving as guides for X-ray or fluoroscopy images. The length of the K-wire in the present wire probe 12 will depend on the purpose for which the probe is being used; it will be cut longer for less invasive procedures, such as lumbar spine procedures and stimulating pedical screws, and shorter for more invasive ones, such as lumbar discectomies and fusions with pedical screws, and still shorter probes for stimulating pedical screws in the thoracic and cervical areas. Another advantage of the present probe system is that handle 14 and cable 16 can be used with different lengths of probes 12 allowing for a kit to be developed of at least one handle 14, at least one cable 16 and a range of probe wires 12 of different lengths.

Figure 2:
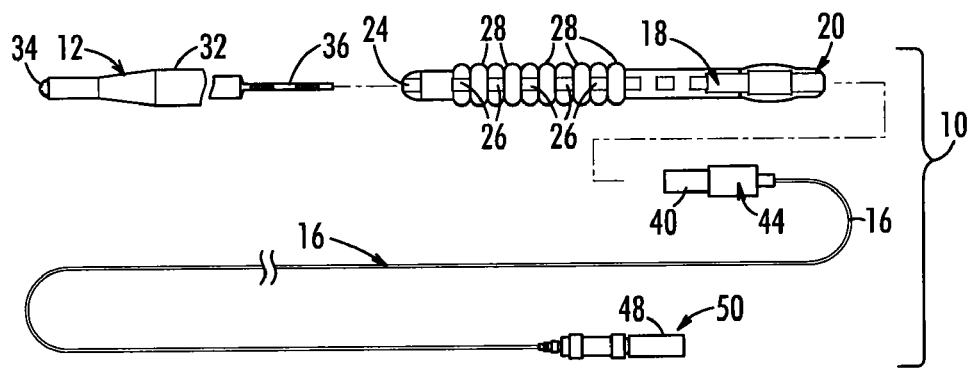
FIG. 2 is an exploded view of a probe system, according to a preferred embodiment of the present invention.

Wire probe 12 has a sensor tip 34 at a first end (see FIG. 5) and an opposing, second end 36 (see FIG. 2). The insulation layer 32 toward sensor tip 34 is tapered ending just short of the sensor tip 34, and also having a short section of uninsulated conductor 30 at adaptor end 36 to for electrical contact when seated in adaptor 40. Probe tip 34 may be hemispherical in shape and may have a diameter of 1.6 mm, a radius of curvature of 0.8 mm. In addition, the very end of probe 12 may be slightly flattened. Other shapes for probe tip 34 are possible depending on the specific preference of the surgeon for the type of use contemplated, such as, for example, a ball tip and a tip with an angled face. A kit as described above may include probe wires with differently shaped tips, too. Insulating layer 32 ends short of second end 36 and may have approximately 11.25 mm free of insulation at 30. Overall wire probe 12 may be 10-35 cm long.

Cable 16 has an adaptor 40 on first end 44 and a connector 48 at a second, opposing end 50; connector 42 may be identical to adaptor 40. Another advantage of the present cable 16 is that either first or second ends 44, 50, respectively, may be plugged into a neuro-monitoring device and the remaining end inserted into handle 14. The exterior shape of adaptor 40 (or connector 50), having enlarged portions, is the same shape as shaped portion 18 of channel 20 so that adaptor 40 fits snuggly into shaped portion 18 and handle 14 holds adaptor 40 securely in place axially, allowing no movement in the axial direction. Adaptor 40 is inserted from the side of handle 14 because the forces on adaptor, as transmitted from wire probe 12 are axial, and the shape of shaped portion 18 will prevent axial movement but, despite the axial resistance to movement, adaptor 40 is nonetheless easily inserted and removed in the radial direction, that is, from the side.

A comparison of FIGS. 1 and 2 illustrates the assembly of probe system 10. In FIG. 1, handle 14 is shown with adaptor 40 pressed into channel 24 at second end 20 of handle 14 leaving conductor 44 running therefrom to a source of electrical current and a neuro-monitoring device (not shown). FIG. 2 illustrates the second end 36 of wire probe 12 near first end 22 of handle 14, with wire probe 12 being positioned near channel 24 beginning at first end 22 of handle 14 with second end 36 of wire probe 12 being visible through one of the windows 26 in FIG. 1. FIG. 1 illustrates wire conductor 30 fully seated in adaptor 40 and held in place by handle 14, ready for use in surgery.

One of the most important advantages of the present invention is the fact that probe system 10 can be used to temporarily position wire probe 12 within the body, then used to identify neural tissue proximate to sensor tip 34, and then handle 14 can be removed while wire probe 12 remains positioned in the body. Wire probe 12 can guide a dilator or other surgical instrument as the surgeon slides the dilator or other device overtop or along wire probe 12. Then cable 16 can be reconnected to wire probe 14 either by inserting proximal end of wire probe 12 directly into adaptor 40 or alternatively via handle 14, and then resuming stimulation in a continuous or intermittent manner.

Figure 3A:
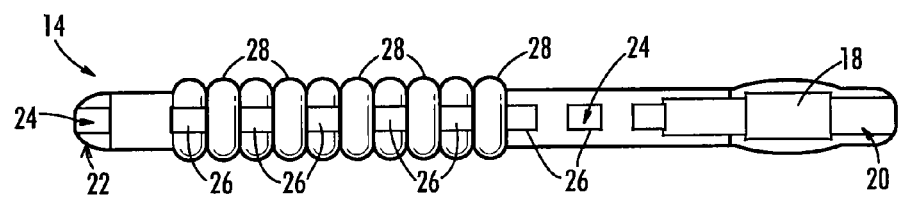
FIGS. 3A, 3B, and 3C show top, bottom, and side views of a handle for use with the present probe system, according to a preferred embodiment of the present invention.
Figure 3B:
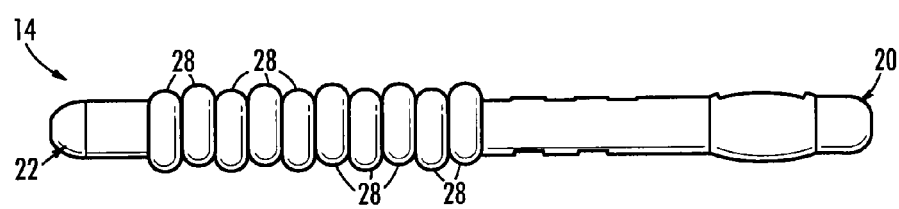
Figure 3C:
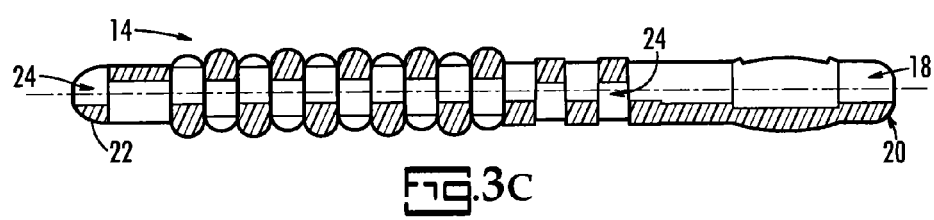
Figure 4:
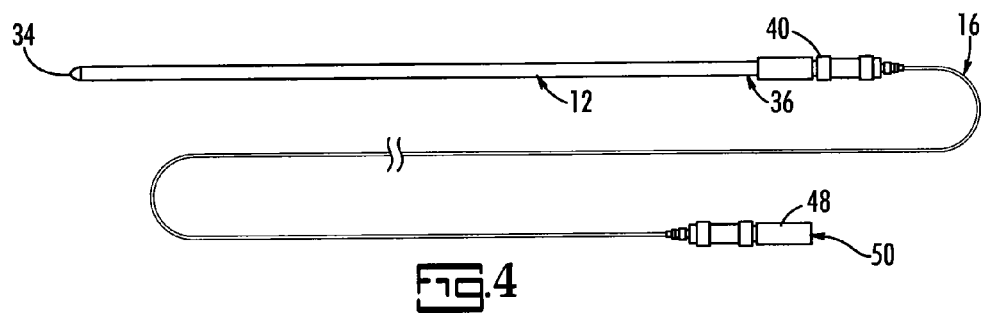
FIG. 4 is a side view of a probe wire and cable without the handle, according to a preferred embodiment of the present invention.

Referring now to FIG. 6, there is shown an alternative embodiment of handle 14, referred to as handle 14' but otherwise equivalent to handle 14 of FIG. 3A and having all the features of handle 14 as shown in FIGS. 3A-3C (and using the same reference numbers used in FIG. 3A in FIG. 6 to indicate those same features). In addition, handle 14' includes a flat terminal 70 for use by a surgeon to tap probe wire 12 into the patient's body. Flat terminal 70 is preferably integrally formed as part of said second end 20 of handle 14' and is approximately 2 centimeters in diameter.

It will be apparent to those skilled in the art of probe design that modifications and substitution can be made to the foregoing preferred embodiments without departing from the spirit of the present invention, which is defined by the appended claim.

What is claimed is:

1. A monopolar probe for use with a neuro-monitoring device, comprising:
   (1) a wire probe comprising an electrically insulated wire having a probe tip at a first end an opposing second end, said second end being free of insulation;
   (2) a cable having a connector at one end to connect said cable to a neuro-monitoring device and an adaptor at an opposing end of said cable, said adaptor dimensioned to receive said second end of said wire; and
   (3) a handle having an exterior surface, a first end, an opposing second end and a side, said handle having a channel formed inside said handle and running from said first end of said handle toward said second end, said channel terminating in a shaped portion toward said second end and open radially to said exterior surface of said side of said handle so that said shaped portion is in communication with said channel and said exterior surface of said handle, said shaped portion adapted to receive said adaptor inserted radially from said exterior surface at said side of said handle, said channel dimensioned to receive said second end of said wire inserted through said channel from said first end of said handle, said adaptor, when in said shaped portion of said handle, preventing further axial movement of said second end of said wire toward said second end of said handle but not preventing axial movement of said wire toward said first end of said handle so that said handle is configured to be removed from said wire probe after said wire probe is inserted into a patient by sliding said wire from said first end of said channel.

2. The monopolar probe as recited in claim 1, wherein said probe tip is shaped in the form of a hemisphere.

3. The monopolar probe as recited in claim 1, wherein said insulation on said first end of said wire tapers toward said wire.

4. The monopolar probe as recited in claim 1, wherein said handle has a window through said exterior surface along said side so that said channel inside said handle is visible from outside said handle.

5. The monopolar probe as recited in claim 1, wherein said handle has plural windows through said exterior surface along said side so that said channel inside said handle is visible from outside said handle.

6. The monopolar probe as recited in claim 1, wherein said handle carries a flat terminal on said second end.

7. A monopolar probe system, comprising:
   (1) an electrically insulated wire having a probe tip at a first end and an opposing second end, said second end being free of insulation;
   (2) a cable having a connector at one end and an adaptor at an opposing end of said cable, said adaptor dimensioned to receive said second end of said wire;
   (3) a handle having an exterior surface, a first end, an opposing second end and a side, said handle having a channel formed inside said handle and running from said first end toward said second end, said channel terminating in a configured portion toward said second end and open radially to said exterior surface of said side of said handle so that said configured portion is in communication with said channel and said exterior surface of said handle, said configured portion adapted to receive said adaptor inserted radially from exterior surface of said side of said handle and said wire being inserted into said channel in said handle, said channel dimensioned to receive said second end of said wire into said channel from said first end of said handle, said adaptor when in said configured portion of said handle, preventing further axial movement of said second end of said wire toward said second end of said handle but not preventing axial movement of said wire toward said first end of said handle so that said handle is configured to be removed and re-attached from said wire probe from said first end of said channel after said wire probe is inserted into a patient; and
   (4) a neuromonitoring device attached to said connector of said cable, said neuromonitoring device adapted to emit a signal to said probe tip via said cable.

8. The monopolar probe system as recited in claim 7, wherein said probe tip is shaped in the form of a hemisphere.

9. The monopolar probe system as recited in claim 7, wherein said first end of said insulation on said wire tapers toward said wire.

10. The monopolar probe system as recited in claim 7, wherein said handle has a window through said exterior surface along said side so that said channel inside said handle is visible from outside said handle.

11. The monopolar probe system as recited in claim 7, wherein said handle has plural windows through said exterior surface along said side so that said channel inside said handle is visible from outside said handle.

12. A monopolar probe system for use with a neuromonitoring device, said probe system comprising:
   (1) an electrically insulated wire having a probe tip at a first end and an opposing second end, said second end being free of insulation;
   (2) a cable having a connector at one end and an adaptor at an opposing end, said adaptor dimensioned to receive said second end of said wire;
   (3) a handle having a long dimension, an exterior surface, a first end, and an opposing second end, said handle having a channel formed inside said handle and running from said first end toward said second end parallel to said long dimension of said handle, said channel terminating in a configured portion toward said second end and open radially to said exterior surface of said handle, said second end of said wire being carrier in said channel, said configured portion being in communication with said channel and said exterior surface of said handle, said configured portion carrying said adaptor, said adaptor receiving said second end of said wire and preventing further axial movement of said second end of said wire toward said second end of said handle but not preventing axial movement of said wire toward said first end of said handle, said connector of said insulated cable configured to be connected to a neuromonitoring device.

13. The probe system as recited in claim 12, further comprising a flat terminal end carried by said second end of said handle for tapping said probe wire into human tissue.

14. The probe system as recited in claim 12, wherein said handle has at least one opening along said radial exterior surface to said channel so that a user can see radially into said channel.

15. The probe system as recited in claim 12, wherein said connector and said adaptor have the same configuration.

16. The probe system as recited in claim 12, wherein said probe wire is K-wire insulated with a polymer.

17. A monopolar probe system for use with a neuromonitoring device, said probe system comprising:
   (1) an insulated K-wire having a shaped probe tip at a first end and an opposing second end, said second end being free of insulation;
   (2) a cable having a connector at one end and an adaptor at an opposing end;

(3) a handle having a radial side, an exterior surface, a first end, and an opposing second end, said handle having a channel formed inside said handle, said channel carrying said second end of said K-wire and running from said first end toward said second end of said handle, said channel terminating near said second end of said handle in a portion holding said adaptor, said portion open to said exterior surface of said radial side of said handle, said second end of said K-wire being seated in said adaptor, said adaptor preventing further axial movement of said second end of said K-wire toward said second end of said handle but not preventing axial movement of said K-wire toward said first end of said handle.

18. The probe system of claim 17, wherein said probe tip has a diameter of 1.6 mm and a radius of curvature of 0.8 mm.

* * * * *